United States Patent
Wu

(10) Patent No.: US 8,623,992 B2
(45) Date of Patent: *Jan. 7, 2014

(54) POLYALKYLENE GLYCOL ESTER INTERMEDIATE TRANSFER MEMBERS

(75) Inventor: Jin Wu, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 235 days.

This patent is subject to a terminal disclaimer.

(21) Appl. No.: 13/084,916

(22) Filed: Apr. 12, 2011

(65) Prior Publication Data
US 2012/0264969 A1    Oct. 18, 2012

(51) Int. Cl.
*C08G 69/08* (2006.01)
*C07C 67/02* (2006.01)
*H01B 1/06* (2006.01)

(52) U.S. Cl.
USPC ............................ 528/310; 560/263; 252/511

(58) Field of Classification Search
None
See application file for complete search history.

(56) References Cited

U.S. PATENT DOCUMENTS

| | | | |
|---|---|---|---|
| 5,487,707 A | 1/1996 | Sharf et al. | |
| 6,139,784 A | 10/2000 | Oshima et al. | |
| 6,318,223 B1 | 11/2001 | Yu et al. | |
| 6,397,034 B1 | 5/2002 | Tarnawskyj et al. | |
| 6,440,515 B1 | 8/2002 | Thornton et al. | |
| 6,602,156 B2 | 8/2003 | Schlueter, Jr. | |
| 7,031,647 B2 | 4/2006 | Mishra et al. | |
| 7,130,569 B2 | 10/2006 | Goodman et al. | |
| 7,139,519 B2 | 11/2006 | Darcy, III et al. | |
| 2001/0016531 A1* | 8/2001 | Morikoshi et al. | 474/237 |
| 2006/0009555 A1* | 1/2006 | Haubennestel et al. | 524/261 |
| 2007/0147914 A1* | 6/2007 | Takahashi et al. | 399/329 |
| 2008/0051303 A1* | 2/2008 | Brand et al. | 508/100 |
| 2008/0114110 A1* | 5/2008 | Lee et al. | 524/366 |
| 2012/0301417 A1* | 11/2012 | Pays et al. | 424/70.7 |

FOREIGN PATENT DOCUMENTS

| | | | |
|---|---|---|---|
| JP | 2006083307 | * | 3/2006 |
| JP | 2008156425 | * | 7/2008 |

OTHER PUBLICATIONS

Database Caplus Chemical Abstracts Service, Columbus, Ohio, US; Database Accession No. 2006:293194, Abstract of JP 2006083307, Nagaya et al., Mar. 30, 2006.*
Database Caplus Chemical Abstracts Service, Columbus, Ohio, US; Database Accession No. 2008:829259, Abstract of JP 2008156425, Shimizu et al., Jul. 10, 2008.*
Machine Translation of JP 2006083307.*

* cited by examiner

*Primary Examiner* — Karl J Puttlitz
(74) *Attorney, Agent, or Firm* — Eugene O. Palazzo

(57) ABSTRACT

An intermediate transfer member includes a mixture of a polyimide, a polyalkylene glycol ester, an optional polysiloxane, and an optional conductive filler component.

14 Claims, 1 Drawing Sheet

POLYALKYLENE GLYCOL ESTER INTERMEDIATE TRANSFER MEMBERS

This disclosure is generally directed to a polyalkylene glycol ester containing intermediate transfer member, and to an intermediate transfer member that includes a mixture of a polyimide, a polyalkylene glycol ester, an optional polysiloxane, and an optional conductive component.

BACKGROUND

Intermediate transfer members, such as intermediate transfer belts selected for transferring a developed image in xerographic systems, are known. For example, there are known intermediate transfer members that include materials with characteristics that cause these members to become brittle, resulting in inadequate acceptance of the developed image and subsequent partial transfer of developed xerographic images to a substrate like paper.

A disadvantage relating to the preparation of an intermediate transfer member is that there is usually deposited a separate release layer that is present on a metal substrate. Thereafter, there is applied to the release layer the intermediate transfer member components, and where the release layer allows the components to be separated from the member by peeling or by the use of mechanical devices. The intermediate transfer member can be in the form of a film, which can be selected for xerographic imaging systems, or the film can be deposited on a supporting substrate like a polymer layer. The use of a release layer adds to the cost and time of preparation, and such a layer can modify a number of the intermediate transfer member characteristics.

There is a need for intermediate transfer members that substantially avoid or minimize the disadvantages of a number of known intermediate transfer members.

There is a need for intermediate transfer member materials that possess self release characteristics from a number of substrates that are selected when such members are prepared.

Also, there is a need for intermediate transfer members that retain their flatness characteristics with minimal or no curl, and where the surface of the member is smooth with minimal rugged peaks and valleys.

Moreover, there is a need for intermediate transfer members with excellent wear and acceptable abrasion resistance, and which members possess improved stability with no or minimal degradation for extended time periods.

Another need relates to intermediate transfer members that have excellent conductivity or resistivity, and that possess acceptable humidity insensitivity characteristics leading to developed images with minimal resolution issues.

These and other needs are achievable in embodiments with the intermediate transfer members and components thereof disclosed herein.

SUMMARY

Disclosed is an intermediate transfer member comprising a polyalkylene glycol ester.

There is illustrated herein an intermediate transfer member comprising a mixture of a polyimide, a polyalkylene glycol ester, a polysiloxane, and a conductive filler component, and wherein said polyalkylene glycol ester is selected from the group consisting of those compounds as represented by the following formulas/structures

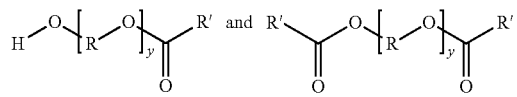

wherein R is alkylene with from about 2 to about 12 carbon atoms, each R' is independently alkyl with from about 4 to about 20 carbon atoms, and y is the number of repeating units of from about 3 to about 100.

There is illustrated herein an intermediate transfer member comprising a mixture of a polyimide, a polyalkylene glycol ester release agent, an optional polysiloxane, and an optional conductive filler component, and wherein said member possesses self-release characteristics from metal substrates.

FIGURES

The following Figures are provided to further illustrate the intermediate transfer members disclosed herein.

EMBODIMENTS

There is provided herein an intermediate transfer member comprising a polyalkylene glycol ester, such as a polyethylene glycol dilaurate. The polyalkylene glycol ester enables or assists in enabling self release from substrates like metal substrates, such as stainless steel, thereby avoiding the need for a separate release layer on the substrate.

More particularly, there is provided herein an intermediate transfer member comprising a mixture of a polyimide, a polyalkylene glycol ester that enables or assists in enabling self release from a substrate like a metal substrate, such as stainless steel, and where there is avoided the need for a separate release layer on the substrate.

Figure 1:
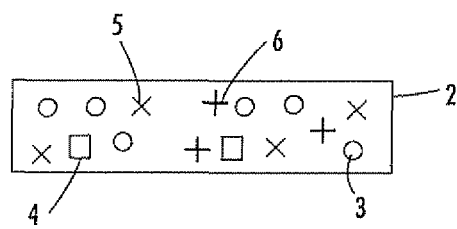
FIG. 1 illustrates an exemplary embodiment of a one layer intermediate transfer member of the present disclosure.

In FIG. 1 there is illustrated an intermediate transfer member comprising a layer 2 comprised of a polyalkylene glycol ester 4, or a mixture of a polyimide 3, a polyalkylene glycol ester 4, an optional siloxane polymer 5, and an optional conductive component 6.

Figure 2:
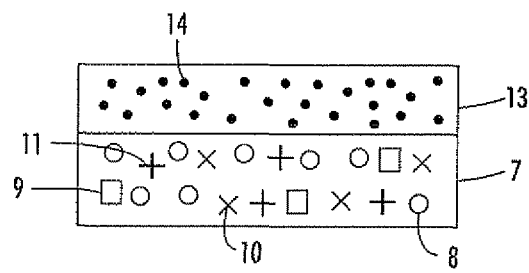
FIG. 2 illustrates an exemplary embodiment of a two layer intermediate transfer member of the present disclosure.

In FIG. 2 there is illustrated a two-layer intermediate transfer member comprising a bottom layer 7 comprising a mixture of a polyimide 8, a polyalkylene glycol ester 9, an optional siloxane polymer 10, and an optional conductive component 11, and an optional top or outer toner release layer 13 comprising release components 14.

Figure 3:
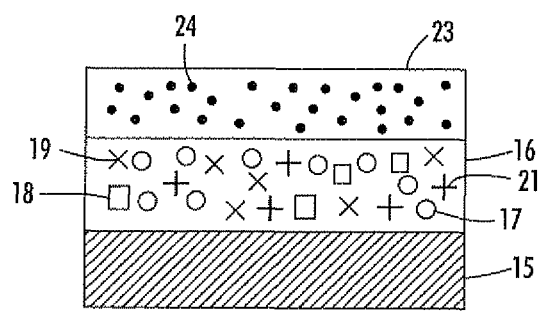
FIG. 3 illustrates an exemplary embodiment of a three layer intermediate transfer member of the present disclosure.

In FIG. 3 there is illustrated a three layer intermediate transfer member comprising a supporting substrate 15, a layer thereover 16 comprising a mixture of a thermosetting polyimide 17, a polyalkylene glycol ester 18, an optional siloxane polymer 19, and an optional conductive component 21, and an optional release layer 23 comprising release components 24.

There is disclosed a self-releasing intermediate transfer member that generally comprises a polyalkylene glycol ester, such as a polyethylene glycol dilaurate, a polyethylene glycol di(2-ethylhexonate), or mixtures thereof. In embodiments, the polyalkylene glycol ester can be mixed with a polymer material to form an intermediate transfer member layer. Thus, in particular embodiments, there is disclosed a self-releasing intermediate transfer member that generally comprises a polyimide, a polyalkylene glycol ester that primarily functions as an internal release agent, a polysiloxane polymer and a conductive component like carbon black, and which member has excellent release and stability characteristics, smooth high quality surfaces, and improved mechanical properties.

The intermediate transfer members disclosed herein exhibit self-release characteristics, and where the use of an external release layer present on, for example, a stainless steel substrate is avoided; have excellent mechanical strength while permitting the rapid and complete transfer of from about 90 to about 99 percent, or from about 95 to about 100 percent transfer of a xerographic developed image; possess a Young's modulus of, for example, from about 3,000 to about 7,000 Mega Pascals (MPa), from about 3,600 to about 6,000 MPa, from about 3,500 to about 5,000 MPa, or from about 3,700 to about 4,000 MPa; have a high glass transition temperature ($T_g$) of from about 200° C. to about 400° C., or from about 275° C. to about 350° C.; a CTE (coefficient of thermal expansion) of from about 20 to about 70 parts per million per degree Kelvin (ppm/° K), or from about 30 to about 60 ppm/° K; and an excellent resistivity as measured with a known High Resistivity Meter of, for example, from about $10^8$ to about $10^{13}$ ohm/square, from about $10^9$ to about $10^{13}$ ohm/square, from about $10^9$ to about $10^{12}$ ohm/square, or from about $10^{10}$ to about $10^{12}$ ohm/square.

Self-release characteristics without the assistance of any external sources, such as prying devices, permit the efficient, economical formation and full separation, from about 95 to about 100 percent, or from about 97 to about 99 percent, of the disclosed intermediate transfer member films from substrates, such as steel, upon which the members are initially prepared, and where release materials and separate release layers can be avoided on the metal substrates. The time period to obtain the self-release characteristics varies depending, for example, on the components selected for the polyalkylene glycol ester containing mixtures disclosed. Generally, however, this time period is from about 1 to about 60 seconds, from about 1 to about 35 seconds, from about 1 to about 10 seconds, or from 1 to about 5 seconds, and in some instances less than about 1 second.

The intermediate transfer members of the present disclosure can be provided in any of a variety of configurations, such as a one-layer configuration, or in a multi-layer configuration including, for example, a top release layer. More specifically, the final intermediate transfer member may be in the form of an endless flexible belt, a web, a flexible drum or roller, a rigid roller or cylinder, a sheet, a drelt (a cross between a drum and a belt), a seamless belt, that is with an absence of any seams or visible joints in the members, and the like.

As disclosed herein, the intermediate transfer member generally comprises a polymer layer formed from a polyalkylene glycol ester, or generated from a mixture of materials comprising at least a polyalkylene glycol ester. In embodiments, the polyalkylene glycol ester can be mixed with a polymer material, such as a polyimide polymer material or precursor thereof, other optional materials, such as a polysiloxane polymer, a conductive component, and the like.

Polyalkylene Glycol Esters

The polyalkylene glycol esters selected for the disclosed intermediate transfer members assist in imparting, or provide self-release characteristics to the material. As such, when the intermediate transfer member is formed on an underlying substrate, the intermediate transfer member will self-release from the substrate.

Examples of polyalkylene glycol esters selected for the intermediate transfer members illustrated herein, and for the intermediate transfer member mixtures, and which esters primarily function as an release agent, are polyalkylene glycol esters selected from the group consisting of those compounds or mixtures thereof as represented by the following formulas/structures

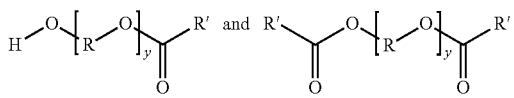

wherein R is an alkylene with, for example, from about 1 to about 18 carbon atoms, from about 2 to about 15 carbon atoms, from about 2 to about 12 carbon atoms, from about 2 to about 10 carbon atoms, from about 3 to about 8 carbon atoms, from about 2 to about 7 carbon atoms, or from about 2 to about 6 carbon atoms, such as methylene, ethylene, propylene, butylene, pentylene, hexylene, heptylene, octylene, nonylene, pentylene, and the like; each R' is independently alkyl with, for example, from about 1 to about 24 carbon atoms, from about 4 to about 20 carbon atoms, from about 6 to about 18 carbon atoms, or from about 6 to about 16 carbon atoms, such as methyl, ethyl, propyl, butyl, pentyl, hexyl, heptyl, octyl, nonyl, decyl, and the like; and y represents the number of repeating segments or units, and is, for example, from about 1 to about 150, from about 2 to about 100, from about 3 to about 100, from about 10 to about 90, from about 25 to about 75, or from about 5 to about 50. The alkylene and alkyl groups can be straight or branched.

Polyalkylene glycol esters selected for the intermediate transfer members illustrated herein, and commercially available from Unitex Chemical Company, include a polyethylene glycol dilaurate, such as UNIPLEX® 810, with a weight average molecular weight of about 964, and a polyethylene glycol di(2-ethylhexoate), such as UNIPLEX® 809, with a weight average molecular weight of about 952. Other polyalkylene glycol esters selected for the intermediate transfer members illustrated herein, and commercially available from BASF, include polyethylene glycol monolaurate (MAPEG® 200ML), polyethylene glycol monostearate (MAPEG® 600MS), polyethylene glycol monooleate (MAPEG® 400MO), polyethylene glycol monotallate (MAPEG® 400MOT), polyethylene glycol distearate (MAPEG® 600DS, 6000DS), polyethylene glycol dioleate (MAPEG® 400DO, 600DO), polyethylene glycol ditallate (MAPEG® 400DOT, 600DOT), MAPEG® L61 dioleate, and the like, and mixtures thereof.

The polyalkylene glycol esters can be present in the intermediate transfer member in various suitable and effective amounts, for enabling or assisting in enabling self release from substrates, inclusive of the ratios as illustrated herein. Various effective amounts of the polyalkylene glycol ester, such as for example, less than about 0.5 weight percent, and more specifically, from about from about 0.1 to about 0.4 weight percent can be selected for the disclosed intermediate transfer member mixtures with the total of ingredients in the mixture being about 100 percent. In embodiments, the polyalkylene glycol ester can be present in the intermediate transfer mixture in an amount of from about 0.1 to about 10 weight percent, from about 1 to about 5 weight percent, from about 0.5 to about 10 weight percent, from about 0.1 to about 5 weight percent, from about 0.5 to about 10 weight percent, from about 0.5 to about 3 weight percent, from about 0.5 to about 2 weight percent, and from about 0.2 to about 3 weight percent, with the total of ingredients in the mixture being about 100 percent.

Polyimide Polymers

The intermediate transfer member can also generally comprise a polymeric film-forming material. Any suitable polymeric film-forming material can be used, such as a polyimide, for the intermediate transfer members disclosed herein.

Examples of the polyimides that can be included in the intermediate transfer member mixture of the polyimide, the polyalkylene glycol ester, the optional polysiloxane, and the optional conductive filler component include known low temperature, and rapidly cured polyimide polymers, such as VTEC™ PI 1388, 080-051, 851, 302, 203, 201, and PETI-5, all available from Richard Blaine International, Incorporated, Reading, Pa. These thermosetting polyimides can be cured at temperatures of from about 180° C. to about 260° C. over a short period of time, such as from about 10 to about 120 minutes, or from about 20 to about 60 minutes, and generally have a number average molecular weight of from about 5,000 to about 500,000 or from about 10,000 to about 100,000, and a weight average molecular weight of from about 50,000 to about 5,000,000 or from about 100,000 to about 1,000,000 as determined by GPC analysis.

Also, for the intermediate transfer member mixture there can be selected thermosetting polyimides that can be cured at temperatures above 300° C., such as PYRE M.L.® RC-5019, RC 5057, RC-5069, RC-5097, RC-5053, and RK-692, all commercially available from Industrial Summit Technology Corporation, Parlin, N.J.; RP-46 and RP-50, both commercially available from Unitech LLC, Hampton, Va.; DURIMIDE® 100, commercially available from FUJIFILM Electronic Materials U.S.A., Inc., North Kingstown, R.I.; and KAPTON® HN, VN and FN, all commercially available from E.I. DuPont, Wilmington, Del.

Additionally, suitable polyimides that may be selected for the disclosed intermediate transfer member mixtures are known thermosetting polyimides formed from the imidization, by heating and curing of a polyamic acid, or a polyimide precursor. Examples of these thermosetting polyimides include the imidization of at least one of a polyamic acid of pyromellitic dianhydride/4,4'-oxydianiline, a polyamic acid of pyromellitic dianhydride/phenylenediamine, a polyamic acid of biphenyl tetracarboxylic dianhydride/4,4'-oxydianiline, a polyamic acid of biphenyl tetracarboxylic dianhydride/phenylenediamine, a polyamic acid of benzophenone tetracarboxylic dianhydride/4,4'-oxydianiline, a polyamic acid of benzophenone tetracarboxylic dianhydride/4,4'-oxydianiline/phenylenediamine, and the like, and mixtures thereof. The heating and curing may be at temperatures that are suitable to cause the imidization of the polyamic acid, which temperature is believed to be from about 235° C. to about 370° C., from about 260° C. to about 350° C., or from about 275° C. to about 330° C.

Commercially available examples of polyamic acids of pyromellitic dianhydride/4,4'-oxydianilines are PYRE-ML RC5019 (about 15 to about 17 weight percent in N-methyl-2-pyrrolidone, NMP), RC5057 (about 14.5 to about 15.5 weight percent in NMP/aromatic hydrocarbon, ratio of 80/20), and RC5083 (about 18 to about 19 weight percent in NMP/DMAc, ratio of 15/85), all obtainable from Industrial Summit technology Corporation, Parlin, N.J.; and DURIMIDE® 100, commercially available from FUJIFILM Electronic Materials U.S.A., Inc.

Examples of polyamic acids of biphenyl tetracarboxylic dianhydride/4,4'-oxydianilines that may be selected for the generation of the polyimides for the disclosed intermediate transfer members include U-VARNISH A, and VARNISH S (about 20 weight percent in NMP), both available from UBE America Inc., New York, N.Y. Polyamic acids of biphenyl tetracarboxylic dianhydride/phenylenediamine examples include PI-2610 (about 10.5 weight percent in NMP), and PI-2611 (about 13.5 weight percent in NMP), both available from HD MicroSystems, Parlin, N.J.

Further examples of polyimides that may be selected for the disclosed intermediate transfer member mixtures can be obtained from the curing at temperatures of from about 260° C. to about 325° C., of polyamic acids of benzophenone tetracarboxylic dianhydride/4,4'-oxydianilines, such as RP46 and RP50 (about 18 weight percent in NMP), both available from Unitech Corp., Hampton, Va. Commercially obtainable from HD MicroSystems, Parlin, N.J., examples of polyamic acids of benzophenone tetracarboxylic dianhydride/4,4'-oxydianiline/phenylenediamines that can be selected are PI-2525 (about 25 weight percent in NMP), PI-2574 (about 25 weight percent in NMP), PI-2555 (about 19 weight percent in NMP/aromatic hydrocarbon, ratio of 80/20), and PI-2556 (about 15 weight percent in NMP/aromatic hydrocarbon/propylene glycol methyl ether, ratio of 70/15/15).

Examples of polyamic acids or esters of polyamic acid that can be imidized by curing can be generated by the reaction of a dianhydride and a diamine. Suitable dianhydrides selected for the reaction include aromatic dianhydrides and aromatic tetracarboxylic acid dianhydrides such as, for example, 9,9-bis(trifluoromethyl)xanthene-2,3,6,7-tetracarboxylic acid dianhydride, 2,2-bis(3,4-dicarboxyphenyl)hexafluoropropane dianhydride, 2,2-bis(3,4dicarboxyphenoxy)phenyl)hexafluoropropane dianhydride, 4,4'-bis(3,4-dicarboxy-2,5,6-trifluorophenoxy)octafluorobiphenyl dianhydride, 3,3',4,4'-tetracarboxybiphenyl dianhydride, 3,3',4,4'-tetracarboxybenzophenone dianhydride, di-(4-(3,4-dicarboxyphenoxy)phenyl)ether dianhydride, di-(4-(3,4-dicarboxyphenoxy)phenyl)sulfide dianhydride, di-(3,4-dicarboxyphenyl)methane dianhydride, di-(3,4-dicarboxyphenyl)ether dianhydride, 1,2,4,5-tetracarboxybenzene dianhydride, 1,2,4-tricarboxybenzene dianhydride, butanetetracarboxylic dianhydride, cyclopentanetetracarboxylic dianhydride, pyromellitic dianhydride, 1,2,3,4-benzenetetracarboxylic dianhydride, 2,3,6,7-naphthalenetetracarboxylic dianhydride, 1,4,5,8-naphthalenetetracarboxylic dianhydride, 1,2,5,6-naphthalenetetracarboxylic dianhydride, 3,4,9,10-perylenetetracarboxylic dianhydride, 2,3,6,7-anthracene tetracarboxylic dianhydride, 1,2,7,8-phenanthrenetetracarboxylic dianhydride, 3,3',4,4'-biphenyltetracarboxylic dianhydride, 2,2',3,3'-biphenyltetracarboxylic dianhydride, 3,3',4-4'-benzophenonetetracarboxylic dianhydride, 2,2',3,3'-benzophenonetetracarboxylic dianhydride, 2,2-bis(3,4-dicarboxyphenyl)propane dianhydride, 2,2-bis(2,3-dicarboxyphenyl)propane dianhydride, bis(3,4-dicarboxyphenyl)ether dianhydride, bis(2,3-dicarboxyphenyl)ether dianhydride, bis(3,4-dicarboxyphenyl)sulfone dianhydride, bis(2,3-dicarboxyphenyl)sulfone 2,2-bis(3,4-dicarboxyphenyl)-1,1,1,3,3,3-hexafluoropropane dianhydride, 2,2-bis(3,4-dicarboxyphenyl)-1,1,1,3,3,3-hexachloropropane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, 4,4'-(p-phenylenedioxy)diphthalic dianhydride, 4,4'-(m-phenylenedioxy)diphthalic dianhydride, 4,4'-diphenylsulfidedioxybis(4-phthalic acid)dianhydride, 4,4'-diphenylsulfonedioxybis(4-phthalic acid)dianhydride, methylenebis(4-phenyleneoxy-4-phthalic acid)dianhydride, ethylidenebis(4-phenyleneoxy-4-phthalic acid)dianhyd ride, isopropylidenebis-(4-phenyleneoxy-4-phthalic acid)dianhydride, hexafluoroisopropylidenebis(4-phenyleneoxy-4-phthalic acid)dianhydride, and the like.

Exemplary diamines selected for the reaction with the dianhydrides include 4,4'-bis-(m-aminophenoxy)-biphenyl, 4,4'-bis-(m-aminophenoxy)-diphenyl sulfide, 4,4'-bis-(m-aminophenoxy)-diphenyl sulfone, 4,4'-bis-(p-aminophenoxy)-benzophenone, 4,4'-bis-(p-aminophenoxy)-diphenyl sulfide, 4,4'-bis-(p-aminophenoxy)-diphenyl sulfone, 4,4'-diamino-azobenzene, 4,4'-diaminobiphenyl, 4,4'-diaminodiphenylsulfone, 4,4'-diamino-p-terphenyl, 1,3-bis-(gamma-aminopropyl)-tetramethyl-disiloxane, 1,6-diaminohexane, 4,4'-d iaminodiphenylmethane, 3,3'-diaminodiphenylmethane, 1,3-diaminobenzene, 4,4'-diaminodiphenylether, 2,4'-diaminodiphenylether, 3,3'-diaminodiphenylether, 3,4'-diaminodiphenylether, 1,4-diaminobenzene, 4,4'-diamino-2,2',3,3',5,5',6,6'-octafluoro-biphenyl, 4,4'-diamino-2,2',3,3',5,5',6,6'-octafluorodiphenylether, bis[4-(3-aminophenoxy)-phenyl]sulfide, bis[4-(3-aminophenoxy)phenyl]sulfone, bis[4-(3-aminophenoxy)phenyl]ketone, 4,4'-bis(3-aminophenoxy)biphenyl, 2,2-bis[4-(3-aminophenoxy)phenyl]-propane, 2,2-bis[4-(3-aminophenoxy)phenyl]-1,1,1,3,3,3-hexafluoropropane, 4,4'-diaminodiphenyl sulfide, 4,4'-diaminodiphenylether, 4,4'-diaminodiphenyl sulfone, 4,4'-diaminodiphenylmethane, 1,1-di(p-aminophenyl)ethane, 2,2-di(p-aminophenyl)propane, and 2,2-di(p-aminophenyl)-1,1,1,3,3,3-hexafluoropropane, and the like, and mixtures thereof.

The dianhydride and diamine reactants can be selected in various suitable amounts, such as for example in a weight ratio of dianhydride to diamine of from about 20:80 to about 80:20, from about 40/60 to about 60/40, or about a 50/50 weight ratio.

The polyimide or a precursor thereof can be present in the intermediate transfer member mixture in the ratios as illustrated herein, and in various effective amounts, such as for example, from about 70 to about 97 weight percent, from about 70 to about 95 weight percent, from about 75 to about 95 weight percent, or from about 80 to about 90 weight percent, with the total of ingredients in the mixture being about 100 percent.

Optional Polysiloxane Polymers

The intermediate transfer member mixture can also include an optional polysiloxane polymer. Examples of polysiloxane polymers selected for the intermediate transfer member mixture disclosed herein include known suitable polysiloxanes, such as a polyether modified polydimethylsiloxane, commercially available from BYK Chemical as BYK® 333, BYK® 330 (about 51 weight percent in methoxypropylacetate), and BYK® 344 (about 52.3 weight percent in xylene/isobutanol, ratio of 80/20); BYK®-SILCLEAN 3710 and BYK® 3720 (about 25 weight percent in methoxypropanol); a polyester modified polydimethylsiloxane, commercially available from BYK Chemical as BYK® 310 (about 25 weight percent in xylene) and BYK® 370 (about 25 weight percent in xylene/alkylbenzenes/cyclohexanone/monophenylglycol, ratio of 75/11/7/7); a polyacrylate modified polydimethylsiloxane, commercially available from BYK Chemical as BYK®-SILCLEAN 3700 (about 25 weight percent in methoxypropylacetate); a polyester polyether modified polydimethylsiloxane, commercially available from BYK Chemical as BYK® 375 (about 25 weight percent in di-propylene glycol monomethyl ether); and the like, and mixtures thereof.

The polysiloxane polymer, or copolymers thereof can be present in the intermediate transfer member mixture in various effective amounts, such as from about 0.01 to about 1 weight percent, from about 0.05 to about 1 weight percent, from about 0.05 to about 0.5 weight percent, from about 0.1 to about 0.3 weight percent, or less than about 0.1 weight percent, with the total of ingredients in the mixture being about 100 percent.

Optional Fillers

Optionally, the intermediate transfer member may contain one or more fillers to, for example, alter and adjust the conductivity of the intermediate transfer member. When the intermediate transfer member is a one layer structure, the conductive filler can be included in the polyalkylene glycol ester, or in the polyalkylene glycol ester containing mixture disclosed herein. However, where the intermediate transfer member is a multi-layer structure, the conductive filler can be included in one or more layers of the member, such as in the polyalkylene glycol ester, the supporting substrate, the polyalkylene glycol ester mixture layer coated thereon, and in both the supporting substrate and the polyalkylene glycol ester mixture layer.

Any suitable filler can be used that provides the desired results. For example, suitable fillers include carbon blacks, metal oxides, polyanilines, other known suitable fillers, and mixtures of fillers.

Examples of carbon black fillers that can be selected for the intermediate transfer members illustrated herein include special black 4 (B.E.T. surface area=180 $m^2/g$, DBP absorption=1.8 ml/g, primary particle diameter=25 nanometers) available from Evonik-Degussa, special black 5 (B.E.T. surface area=240 $m^2/g$, DBP absorption=1.41 ml/g, primary particle diameter=20 nanometers), color black FW1 (B.E.T. surface area=320 $m^2/g$, DBP absorption=2.89 ml/g, primary particle diameter=13 nanometers), color black FW2 (B.E.T. surface area=460 $m^2/g$, DBP absorption=4.82 ml/g, primary particle diameter=13 nanometers), color black FW200 (B.E.T. surface area=460 $m^2/g$, DBP absorption=4.6 ml/g, primary particle diameter=13 nanometers), all available from Evonik-Degussa; VULCAN® carbon blacks, REGAL® carbon blacks, MONARCH® carbon blacks, and BLACK PEARLS® carbon blacks available from Cabot Corporation. Specific examples of conductive carbon blacks are BLACK PEARLS® 1000 (B.E.T. surface area=343 $m^2/g$, DBP absorption=1.05 ml/g), BLACK PEARLS® 880 (B.E.T. surface area=240 $m^2/g$, DBP absorption=1.06 ml/g), BLACK PEARLS® 800 (B.E.T. surface area=230 $m^2/g$, DBP absorption=0.68 ml/g), BLACK PEARLS® L (B.E.T. surface area=138 $m^2/g$, DBP absorption=0.61 ml/g), BLACK PEARLS® 570 (B.E.T. surface area=110 $m^2/g$, DBP absorption=1.14 ml/g), BLACK PEARLS® 170 (B.E.T. surface area=35 $m^2/g$, DBP absorption=1.22 ml/g), VULCAN® XC72 (B.E.T. surface area=254 $m^2/g$, DBP absorption=1.76 ml/g), VULCAN® XC72R (fluffy form of VULCAN® XC72), VULCAN® XC605, VULCAN® XC305, REGAL® 660 (B.E.T, surface area=112 $m^2/g$, DBP absorption=0.59 ml/g), REGAL® 400 (B.E.T. surface area=96 $m^2/g$, DBP absorption=0.69 ml/g), REGAL® 330 (B.E.T. surface area=94 $m^2/g$, DBP absorption=0.71 ml/g), MONARCH® 880 (B.E.T. surface area=220 $m^2/g$, DBP absorption=1.05 ml/g, primary particle diameter=16 nanometers), and MONARCH® 1000 (B.E.T. surface area=343 $m^2/g$, DBP absorption=1.05 ml/g, primary particle diameter=16 nanometers); and Channel carbon blacks available from Evonik-Degussa. Other known suitable carbon blacks not specifically disclosed herein may be selected as the filler or conductive component for the intermediate transfer members disclosed herein.

Examples of polyaniline fillers that can be selected for incorporation into the intermediate transfer members are PANIPOL™ F, commercially available from Panipol Oy, Finland; and known lignosulfonic acid grafted polyanilines. These polyanilines usually have a relatively small particle size diameter of, for example, from about 0.5 to about 5 microns; from about 1.1 to about 2.3 microns; or from about 1.5 to about 1.9 microns.

Metal oxide fillers that can be selected for the disclosed intermediate transfer members include, for example, tin oxide, antimony doped tin oxide, indium oxide, indium tin oxide, zinc oxide, and titanium oxide, and the like.

When present, the filler can be selected in an amount of, for example, from about 1 to about 60 weight percent, from about 3 to about 40 weight percent, from about 4 to about 30 weight percent, from about 10 to about 30 percent, or from about 5 to about 20 weight percent, with the total of ingredients in the mixture being about 100 percent.

Optional Additional Polymers

In embodiments of the present disclosure, the intermediate transfer member mixture can further include an optional polymer that primarily functions as a binder. Examples of suitable additional polymers include a polyamideimide, a polycarbonate, a polyphenylene sulfide, a polyamide, a polysulfone, a polyetherimide, a polyester, a polyvinylidene fluoride, a polyethylene-co-polytetrafluoroethylene, and the like, and mixtures thereof.

When an additional polymer is selected, it can be included in the intermediate transfer member mixture in any desirable and effective amounts. For example, the polymer can be present in an amount of from about 1 to about 75 weight percent, from about 2 to about 45, or from about 3 to about 15 weight percent, with the total of ingredients in the mixture being about 100 percent.

Optional Supporting Substrates

If desired, a supporting substrate can be included in the intermediate transfer member, such as beneath the polyalkylene glycol ester, or beneath the polyalkylene glycol ester mixture layer. The supporting substrate can be included to provide increased rigidity or strength to the intermediate transfer member.

The polyalkylene glycol ester or the coating dispersion of the polyalkylene glycol ester containing mixture can be formed on any suitable supporting substrate material after being self-released from, for example, a stainless steel substrate to form the intermediate transfer member. Exemplary supporting substrate materials include polyimides, polyamideimides, polyetherimides, mixtures thereof, and the like.

More specifically, examples of the intermediate transfer member supporting substrates are polyimides inclusive of known low temperature, and rapidly cured polyimide polymers, such as VTEC™ PI 1388, 080-051, 851, 302, 203, 201, and PETI-5, all available from Richard Blaine International, Incorporated, Reading, Pa., polyamideimides, polyetherimides, and the like The thermosetting polyimides can be cured at temperatures of from about 180° C. to about 260° C. over a short period of time, such as from about 10 to about 120 minutes, or from about 20 to about 60 minutes, and generally have a number average molecular weight of from about 5,000 to about 500,000 or from about 10,000 to about 100,000, and a weight average molecular weight of from about 50,000 to about 5,000,000 or from about 100,000 to about 1,000,000. Also, for the supporting substrate there can be selected thermosetting polyimides that can be cured at temperatures of above 300° C., such as PYRE M.L.® RC-5019, RC-5057, RC-5069, RC-5097, RC-5053, and RK-692, all commercially available from Industrial Summit Technology Corporation, Parlin, N.J.; RP-46 and RP-50, both commercially available from Unitech LLC, Hampton, Va.; DURIMIDE® 100, commercially available from FUJIFILM Electronic Materials U.S.A., Inc., North Kingstown, R.I.; and KAPTON® HN, VN and FN, all commercially available from E.I. DuPont, Wilmington, Del.

Examples of polyamideimides that can be selected as supporting substrates for the intermediate transfer members disclosed herein are VYLOMAX® HR-11NN (15 weight percent solution in N-methylpyrrolidone, $T_g$=300° C., and $M_W$=45,000), HR-12N2 (30 weight percent solution in N-methylpyrrolidone/xylene/methyl ethyl ketone=50/35/15, $T_g$=255° C., and $M_W$=8,000), HR-13NX (30 weight percent solution in N-methylpyrrolidone/xylene=67/33, $T_g$=280° C., and $M_W$=10,000), HR-15ET (25 weight percent solution in ethanol/toluene=50/50, $T_g$=260° C., and $M_W$=10,000), HR-16NN (14 weight percent solution in N-methylpyrrolidone, $T_g$=320° C., and $M_W$=100,000), all commercially available from Toyobo Company of Japan, and TORLON® AI-10 ($T_g$=272° C.), commercially available from Solvay Advanced Polymers, LLC, Alpharetta, Ga.

Examples of specific polyetherimide supporting substrates that can be selected for the intermediate transfer members disclosed herein are ULTEM® 1000 ($T_g$=210° C.), 1010 ($T_g$=217° C.), 1100 ($T_g$=217° C.), 1285, 2100 ($T_g$=217° C.), 2200 ($T_g$=217° C.), 2210 ($T_g$=217° C.), 2212 ($T_g$=217° C.), 2300 ($T_g$=217° C.), 2310 ($T_g$=217° C.), 2312 ($T_g$=217° C.), 2313 ($T_g$=217° C.), 2400 ($T_g$=217° C.), 2410 ($T_g$=217° C.), 3451 ($T_g$=217° C.), 3452 ($T_g$=217° C.), 4000 ($T_g$=217° C.), 4001 ($T_g$=217° C.), 4002 ($T_g$=217° C.), 4211 ($T_9$=217° C.), 8015, 9011 ($T_g$=217° C.), 9075, and 9076, all commercially available from Sabic Innovative Plastics.

Once formed, the supporting substrate can have any desired and suitable thickness. For example, the supporting substrate can have a thickness of from about 10 to about 300 microns, such as from about 50 to about 150 microns, or from about 75 to about 125 microns.

Optional Release Layer

If desired, an optional release layer can be further included in the intermediate transfer member, such as over the polyalkylene glycol ester layer, or deposited on the polyalkylene glycol ester mixtures illustrated herein. The release layer material can assist in providing toner cleaning, and additional effective developed image transfer efficiency from a photoconductor to the intermediate transfer member.

When selected, the release layer can have any desired and suitable thickness. For example, the release layer can have a thickness of from about 1 to about 100 microns, about 10 to about 75 microns, or from about 20 to about 50 microns.

The optional release layer material can comprise TEFLON®-like materials including fluorinated ethylene propylene copolymer (FEP), polytetrafluoroethylene (PTFE), polyfluoroalkoxy polytetrafluoroethylene (PFA TEFLON®), and other TEFLON®-like materials; silicone materials, such as fluorosilicones, and silicone rubbers, such as Silicone Rubber 552, available from Sampson Coatings, Richmond, Va., (polydimethyl siloxane/dibutyl tin diacetate, 0.45 gram DBTDA per 100 grams polydimethyl siloxane rubber mixture, with a molecular weight $M_W$ of approximately 3,500); and fluoroelastomers, such as those sold as VITON®, such as copolymers and terpolymers of vinylidenefluoride, hexafluoropropylene, and tetrafluoroethylene, which are known commercially under various designations as VITON A®, VITON E®, VITON E60C®, VITON E45®, VITON E430®, VITON B910®, VITON GH®, VITON B50®, VITON E45®, and VITON GF®. The VITON® designation is a Trademark of E.I. DuPont de Nemours, Inc. Two known fluoroelastomers are comprised of (1) a class of copolymers of vinylidenefluoride, hexafluoropropylene, and tetrafluoroethylene, known commercially as VITON A®; (2) a class of terpolymers of vinylidenefluoride, hexafluoropropylene, and tetrafluoroethylene, known commercially as VITON B®; and (3) a class of tetrapolymers of vinylidenefluoride, hexafluoropropylene, tetrafluoroethylene, and a cure site monomer, such as VITON GF®, having 35 mole percent of vinylidenefluoride, 34 mole percent of hexafluoropropylene, and 29 mole percent of tetrafluoroethylene with 2 percent cure site monomer. The cure site monomers can be those available from E.I. DuPont de Nemours, Inc. such as 4-bromoperfluorobutene-1,1,1-dihydro-4-bromoperfluorobutene-1,3-bromoperfluoropropene-1,1,1-dihydro-3-bromoperfluoropropene-1, or any other suitable, known, commercially available cure site monomers.

Intermediate Transfer Member Formation

The intermediate transfer members illustrated herein comprising a polyalkylene glycol ester, or comprising a mixture of a polyimide, a polyalkylene glycol ester, a polysiloxane, and an optional conductive filler component, can be formulated into an intermediate transfer member by any suitable method. For example, with known milling processes, uniform dispersions of the intermediate transfer member mixtures can be obtained, and then coated on individual metal substrates, such as a stainless steel substrate or the like, using known draw bar coating or flow coating methods. The resulting individual film or films can be dried at high temperatures, such as by heating the films at from about 100° C. to about 400° C., or from about 160° C. to about 300° C., for a suitable period of time, such as from about 20 to about 180 minutes, or from about 40 to about 120 minutes, while remaining on the substrates. After drying and cooling to room temperature, about 23° C. to about 25° C., the films self release from the steel substrates, that is the films release without any external assistance. The resultant intermediate transfer film product can have a thickness of, for example, from about 15 to about 150 microns, from about 20 to about 100 microns, or from about 25 to about 80 microns.

As metal substrates selected for the deposition of the polyalkylene glycol ester, and for the polyalkylene glycol ester mixtures disclosed herein, there can be selected stainless steel, aluminum, nickel, copper, and their alloys, glass plates, and other conventional typical known materials.

Examples of solvents selected for formation of the intermediate transfer member mixtures, which solvents can be selected in an amount of, for example, from about 60 to about 95 weight percent, or from about 70 to about 90 weight percent of the total mixture components weight include alkylene halides, such as methylene chloride, tetrahydrofuran, toluene, monochlorobenzene, N-methyl-2-pyrrolidone, N,N-dimethylformamide, N,N-dimethylacetamide, methyl ethyl ketone, dimethylsulfoxide (DMSO), methyl isobutyl ketone, formamide, acetone, ethyl acetate, cyclohexanone, acetanilide, mixtures thereof, and the like. Diluents can be mixed with the solvents selected for the intermediate transfer member mixtures. Examples of diluents added to the solvents in amounts of from about 1 to about 25 weight percent, and from 1 to about 10 weight percent, based on the weight of the solvent and the diluent are known diluents like aromatic hydrocarbons, ethyl acetate, acetone, cyclohexanone and acetanilide.

The intermediate transfer members illustrated herein can be selected for a number of printing and copying systems, inclusive of xerographic printing systems. For example, the disclosed intermediate transfer members can be incorporated into a multi-imaging xerographic machine where each developed toner image to be transferred is formed on the imaging or photoconductive drum at an image forming station, and where each of these images is then developed at a developing station, and transferred to the intermediate transfer member. The images may be formed on a photoconductor and developed sequentially, and then transferred to the intermediate transfer member. In an alternative method, each image may be formed on the photoconductor or photoreceptor drum, developed, and then transferred in registration to the intermediate transfer member. In an embodiment, the multi-image system is a color copying system, wherein each color of an image being copied is formed on the photoreceptor drum, developed, and transferred to the intermediate transfer member.

After the toner latent image has been transferred from the photoreceptor drum to the intermediate transfer member, the intermediate transfer member may be contacted under heat and pressure with an image receiving substrate such as paper. The toner image on the intermediate transfer member is then transferred and fixed, in image configuration, to the substrate such as paper.

Specific embodiments will now be described in detail. These examples are intended to be illustrative, and are not limited to the materials, conditions, or process parameters set forth in these embodiments. All parts are percentages by weight of total solids of all the components unless otherwise indicated. The viscosity values were determined by a viscometer.

COMPARATIVE EXAMPLE 1

A coating mixture was prepared by stirring a mixture of special carbon black 4 obtained from Degussa Chemicals, a polyimide of a polyamic acid of pyromellitic dianhydride/4,4'-oxydianiline, available as Pyre-M.L. RC-5019 available from Industrial Summit Technology, and the polyester modified polydimethylsiloxane, available as BYK® 310 available from BYK Chemical, in a ratio of 14/85.95/0.05 based on the initial mixture feed amounts, in N-methyl-2-pyrrolidone, (NMP), about 17 weight solids. The obtained intermediate transfer member dispersion was coated on a stainless steel substrate of a thickness of 0.5 millimeter, and subsequently the mixture was cured by heating at 125° C. for 30 minutes, 190° C. for 30 minutes, and 320° C. for 60 minutes. The resulting intermediate transfer member, about 80 microns in thickness, comprised of the above components in the ratios indicated did not self release from the stainless substrate, but rather adhered to this substrate. After being immersed in water for 3 months, the intermediate transfer member obtained eventually self released from the substrate.

EXAMPLE I

There was prepared by admixing with stirring a coating mixture comprising special carbon black 4 obtained from Degussa Chemical, a polyimide of a polyamic acid of pyromellitic dianhydride/4,4'-oxydianiline, available as Pyre-M.L. RC-5019 from Industrial Summit Technology, 0.5 weight percent of polyethylene glycol dilaurate (UNIPLEX® 810), as obtained from Unitex Chemical, and a polyester modified polydimethylsiloxane BYK® 310, obtained from BYK Chemical, in a ratio of 14/85.45/0.5/0.05 based on the initial mixture feed amounts, in N-methyl-2-pyrrolidone, about 17 weight solids. The obtained intermediate transfer member coating dispersion was coated on a stainless steel substrate of a thickness of 0.5 millimeter, and subsequently the mixture was cured by heating at 125° C. for 30 minutes, 190° C. for 30 minutes, and 320° C. for 60 minutes. The resulting intermediate transfer member film comprised of the above ingredients of special carbon black 4, the polyimide formed from the curing by heating of the intermediate containing mixture of the polyamic acid of pyromellitic dianhydride/4,4'-oxydianiline Pyre-M.L. RC-5019, polyethylene glycol dilaurate (UNIPLEX® 810), and the polyester modified polydimethylsiloxane BYK® 310 in the ratio of 14/85.45/0.5/0.05, immediately self released, within a few seconds, from the stainless steel without the assistance of any external processes.

EXAMPLE II

There is prepared a number of intermediate transfer members by repeating the process of Example I except that the polyethylene glycol dilaurate (UNIPLEX® 810) is replaced with 2 weight percent of one of polyethylene glycol di(2-ethylhexoate) (UNIPLEX® 809), polyethylene glycol monolaurate (MAPEG® 200ML), polyethylene glycol monostearate (MAPEG® 600MS), polyethylene glycol monooleate (MAPEG® 400MO), polyethylene glycol monotallate (MAPEG® 400MOT), polyethylene glycol distearate (MAPEG® 600DS, 6000DS), polyethylene glycol dioleate (MAPEG® 400DO, 600DO), or polyethylene glycol ditallate (MAPEG® 400DOT, 600DOT), MAPEG® L61 dioleate in the ratios of 14/83.95/2/0.05. It is believed that the intermediate transfer member films that result will self release from the stainless steel substrates.

EXAMPLE III

There is prepared a number of intermediate transfer members by repeating the process of Example I except there is selected for the coating composition mixture the polyimde generated from a polyamic acid of biphenyl tetracarboxylic dianhydride/4,4'-oxydianiline (U-VARNISH A obtained from UBE America Inc.), a polyamic acid of biphenyl tetracarboxylic dianhydride/phenylenediamine (PI-2610 obtained from HD MicroSystems), a polyamic acid of benzophenone tetracarboxylic dianhydride/4,4'-oxydianiline (RP50 obtained from Unitech Corp.), or a polyamic acid of benzophenone tetracarboxylic dianhydride/4,4'-oxydianiline/phenylenediamine (PI-2525 obtained from HD MicroSystems). It is believed that the intermediate transfer member films that result will self release from the stainless steel substrates.

MEASUREMENTS

The above intermediate transfer members of Example I, and the Comparative Example 1 were measured for Young's Modulus following the known ASTM D882-97 process. Samples (0.5 inch×12 inch) of each intermediate transfer member were placed in the Instron Tensile Tester measurement apparatus, and then the samples were elongated at a constant pull rate until breaking. During this time, there was recorded the resulting load versus the sample elongation. The Young's Modulus was calculated by taking any point tangential to the initial linear portion of the recorded curve results, and dividing the tensile stress by the corresponding strain. The tensile stress was calculated by the load divided by the average cross sectional area of each of the test samples. The results are provided in Table 1.

The surface resistivity of the above intermediate transfer members of Example I, and Comparative Example 1 was also measured using a High Resistivity Meter, and the results are provided in Table 1.

TABLE 1

| | Surface Resistivity (ohm/sq) | Young's Modulus (MPa) | Release Time From the Metal Substrate |
|---|---|---|---|
| Comparative Example 1 | $1.6 \times 10^{11}$ | 3,400 | Did not release; needs to be immersed in water for 3 months prior to being released. |
| Example I | $7.2 \times 10^{10}$ | 3,500 | Excellent; released in 10 seconds. |

Incorporation of the polyethylene glycol dilaurate into the intermediate transfer member had substantially no negative impacts on both mechanical and electrical properties of the intermediate transfer members of Comparative Example 1 and Example I.

Also, the intermediate transfer member of Example I self released quickly, within 10 seconds, from the substrate without the need to apply an additional release layer on the stainless steel substrate, while the Comparative Example 1 did not self release and remained on the stainless steel substrate, being released only after immersed in water for three months.

After being released from the stainless steel substrate, the Example I and Example II films obtained can be used as intermediate transfer members. Also, the Example I and Example II films obtained can be laminated or deposited on respective supporting substrates of a polymer like a polyimide.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

What is claimed is:

1. An intermediate transfer member comprising a mixture of a polyimide, apolyalkylene glycol ester present in an amount of from about 0.1 to about 5 weight percent and selected from the group consisting of a polyethylene glycol dilaurate, and a polyethylene glycol di(2-ethylhexoate, a polyester modified polydimethylsiloxane, and a conductive carbon black filler component.

2. An intermediate transfer member in accordance with claim 1 wherein said polyalkylene glycol ester is a polyethylene glycol di(2-ethylhexoate.

3. An intermediate transfer member in accordance with claim 1 wherein said poiyalkylene glycol ester is polyethylene glycol dilaurate.

4. An intermediate transfer member in accordance with claim 1 wherein said polyalkylene glycol ester is polyethylene glycol dilaurate present in an amount of about 0.5 weight percent.

5. An intermediate transfer member in accordance with claim 1 wherein the polyalkylene glycol ester is present in an amount of from about 0.5 to about 3 weight percent based on the total of ingredients present in the mixture being about 100 percent.

6. An intermediate transfer member in accordance with claim 1 wherein for each ingredient of the mixture, the polyimide is present in an amount of from about 70 to about 95 weight percent, the polyallcylene glycol ester is present in an amount of from about 0.5 to about 3 weight percent, the polysiloxane is present in an amount of from about 0.05 to about 1 weight percent, and the conductive carbon black filler component is present in an amount of from about 3 to about 40 weight percent, with the total of ingredients being about 100 percent.

7. An intermediate transfer member in accordance with claim 1 wherein the member has a resistivity of from about $10^9$ to about $10^{13}$ ohm/square, and wherein the conductive filler is carbon back.

8. An intermediate transfer member comprising a mixture of a polyimide of a polyamic acid of pyromellitic dianhydride/4,4'-oxydianiline, a polyalkylene glycol ester present in an amount of from about 0.1 to about 5 weight percent and selected from the group consisting of a polyethylene glycol dilaurate, and a polyethylene olycol di(2-ethylhexcate), a polyester modified polydimethylsiloxane, and carbon black.

9. An intermediate transfer member in accordance with claim 8 said polyethylene glycol dilaurate is present in an amount of 0.5 weight percent.

10. An intermediate transfer member in accordance with claim 8 wherein said polyaikylene glycol ester is polyethylene glycol dilaurate.

11. An intermediate transfer member in accordance with claim 8 wherein said poiyalkylene glycol ester is polyethylene glycol di(2-ethylhexoate).

12. A xerographic intermediate transfer member comprised of a mixture of a polyimide, a polyalkylene glycol ester selected from the group consisting of a polyethylene glycol dilaurate, and a polyethylene glycol di(2-ethylgexoate), a polyester modified polydimethylsilaxane, and a carbon black conductive tiller component, wherein for each ingredient of the mixture, the polyimide is present in an amount of from about 70 to about 95 weight percent, the polyalkylene glycol ester is present in an amount of from about 0.1 to at 5 weight percent, the polysiloxane is present in an amount of from about 0.05 to about 1 weight percent, and the carbon black conductiye filler component is present in an amount of from about 3 to about 40 weight percent, with the total of ingredients being about 100 percent.

13. An intermediate transfer member in accordance with claim 12 wherein said polyethylene glycol dilaurate is present in an amount of 0.5 weight percent.

14. An intermediate transfer member in accordance with claim 12 wherein said polyalkylene glycol ester is polyethylene glycol dilaurate and wherein the ratio of said carbon black to said polyimide to said poiyethylene glycol dilaurate to said polysiloxane is 14/85.45/0.5/0.05.

* * * * *